United States Patent [19]
McShane et al.

[11] 4,355,536
[45] Oct. 26, 1982

[54] SLUDGE MEASURING APPARATUS AND ULTRASONIC PROBE ASSEMBLY THEREFOR

[75] Inventors: James L. McShane, Churchill Borough; Leonard R. Golick, Penn Township, Allegheny County; Stanley R. Spiegelman, Pittsburgh, all of Pa.

[73] Assignee: Westinghouse Electric Corp., Pittsburgh, Pa.

[21] Appl. No.: 80,976

[22] Filed: Oct. 2, 1979

[51] Int. Cl.³ .......................................... G01N 29/00
[52] U.S. Cl. ...................... 73/633; 73/290 V
[58] Field of Search ................ 73/632, 633, 641, 618, 73/620, 625, 290 V; 367/908; 310/334, 336

[56] References Cited

U.S. PATENT DOCUMENTS

| | | | |
|---|---|---|---|
| 3,821,834 | 7/1974 | McElroy | 73/632 |
| 3,950,660 | 4/1976 | McElroy | 310/336 |
| 3,987,666 | 10/1976 | Blanc et al. | 73/633 |
| 4,121,094 | 10/1978 | Di Vito et al. | 367/908 |

FOREIGN PATENT DOCUMENTS 1066775 11/1979 Canada ................................. 73/633

*Primary Examiner*—Stephen A. Kreitman
*Attorney, Agent, or Firm*—C. M. Lorin

[57] ABSTRACT

In a steam generator an ultrasonic probe is used to measure the accumulation of sludge between the tubes. A ribbon-like probe carrier is fed into the vessel and deflected by a carriage placed in alignment with a lane of tubes at 90°, the probe head being advanced in the lane to measure vertically and sideways the distance to the surface of the sludge. The probe carrier consists of two steel tapes held face-to-face by a plastic tube which has been heat shrunk. The conductors for the transducers are contained in the space between concave tapes. An adaptor mounted at the end of the probe carrier is amovably connected to the probe head. Probe head, adaptor and probe carrier are sealed so that measurement can be conducted inside the steam generator supposedly filled with water.

19 Claims, 12 Drawing Figures

SLUDGE MEASURING APPARATUS AND ULTRASONIC PROBE ASSEMBLY THEREFOR

BACKGROUND OF THE INVENTION

The present invention relates to instrument mechanisms in general, and more particularly to apparatus for detecting the presence of objects, or material, behind an obstruction.

The invention also relates to measuring apparatus capable of gathering data behind an obstruction.

The invention is applicable to the maintenance of a steam generator, particularly a nuclear power plant steam generator.

A steam generator contains many vertical tubes aligned by rows and columns in close relationship to each other. Material deposits tend to settle and accumulate between the tubes at the bottom, forming a sludge. The sludge has been found to be harmful, especially by causing tube corrosion. As part of a cleaning process for sludge removal, water is projected by lancing between the tubes, which operation can only be completed to satisfaction after a determination has been made of the initial extent of the sludge and of the amount of deposits remaining between the tubes afer lancing.

Accordingly, an object of the present invention is to measure the upper contour of the sludge at the bottom of an array of tubes in a steam generator vessel open for maintenance and cleaning. For this purpose, access into the steam generator vessel must be combined with access into the narrow confines of the tube array. Moreover, measurement of the upper surface of the sludge is most conveniently achieved ultrasonically from above with a probe after the vessel has been partially filled with water, while the immersed probe is being selectively positioned and kept at a definite level in the vessel.

Methods other than ultrasonics can be used in ascertaining sludge amounts between the tubes. However, optical means may be unacceptable in a steam generator environment. Photography does not afford quantitative data. The use of eddy currents generated from the primary side, e.g. inside the tubes, provides only point-by-point data. There is also in the latter case the danger of exposure to radiation for the operator. Balancing water contents may give an indication of the volume of the sludge as a whole, but such method does not reveal the actual distribution of the sludge among the tubes. For this reason, the ultrasonic method is preferred.

SUMMARY OF THE INVENTION

The invention resides in apparatus for bi-dimensionally positioning a probe within an enclosure defined by a surrounding wall. More specifically, the wall is part of a vessel containing water and the probe includes at least one ultrasonic transducer element for measuring distances from each position.

The probe is mounted at the end of a carrier in the form of an elongated member having substantial stiffness longitudinally and vertically while being bendable out of the vertical plane. The apparatus comprises means positioned a distance from the vessel wall along a first horizontal axis for deflecting the probe carrier along a second horizontal axis orthogonally from the first axis, and means for feeding the probe carrier through the deflecting means, thereby to position the probe with the carrier along the second axis.

More specifically, a track and support assembly mounted across the vessel supports a carriage in motion along the first axis. The deflecting means mounted on the carriage are set into position for measurement by stopping the carriage at any point on its track.

The invention is used according to the preferred embodiment, in the measurement of sludge accumulation at the bottom of the tubes of a steam generator. In this context, the probe is specially designed so that with the probe carrier it can pass easily between rows of tubes while measuring ultrasonically the distance to the upper surface of the sludge. Transducer elements mounted at an angle direct ultrasonic signals sideways between the tubes on either side of the tube lane, and an additional transducer element at the same time scans the aligned tubes thereby providing a count indicative of distance of travel. By combining data from an upward and a downward oriented transducer, depths are effectively and accurately measured for successive positions by reference to the level of the water in the vessel.

The carriage is advanced, or brought back, on its track with the assist of an arm accurately marked for implemented positioning from a handhole in the wall of the vessel and toward the center thereof. The probe carrier is fed regularly, taking advantage of electronics in order to derive a distance count automatically correlated with actual measurements derived when the probe is displaced inside a tube lane.

The probe carrier has been designed specially in order to provide stiffness lengthwise, rigidity in the vertical plane and bendability sideways. Built in a ribbon-like fashion, the probe carrier consists of two steel tapes placed side-by-side within a plastic tubing which has been heat-shrunk so as to hold them face-to-face by their concave side. Insulated electrical conductors operative to and from the probe are held in the space between the two tapes. The deflecting means consist of a platform having rollers defining an L-shaped path parallel to the axis of the carriage track axis and to the one in the horizontal plane at a right angle thereto.

DESCRIPTION OF THE PREFERRED EMBODIMENT

For the purpose of illustration, the invention will be described hereinafter as a system for mapping the contour of sludge deposits between tubes at the bottom of a steam generator.

Figure 1:
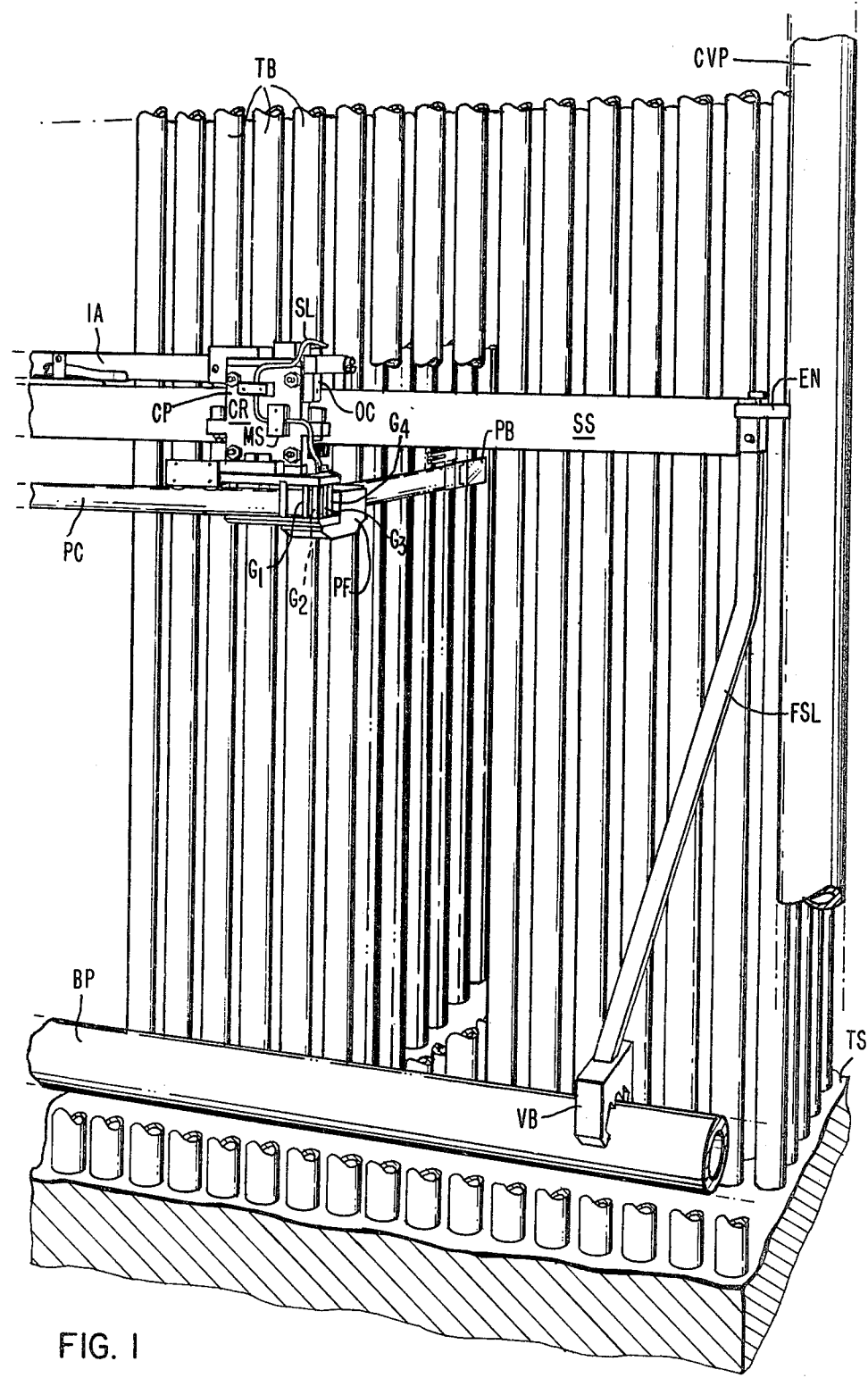
FIG. 1 shows the apparatus according to the present invention installed inside the array of tubes of a steam generator.

Referring to FIG. 1, the steam generator includes a vessel containing water in which is immersed an array of tubes TB. Typically, the steam generator contains seven thousand vertical tubes of 0.875 in. diameter spaced in two directions on a 1.25 in. pitch, approximately. The vertical tubes are associated by pairs with a U-bend at the top (not shown) so as to straddle the two sides of a 3.5 in. aisle extending centrally across the vessel. A 6 in. diameter handhole (not shown) is provided at each of the two opposite ends of the central aisle at for example 21 in. above the tubesheet TS which is at the bottom of the vessel containing the tubes. Foreign deposits from the secondary system remain behind during the steam generation process and settle on the tubesheet TS at the bottom of the array of tubes. When cleaning the steam generator, the vessel is first emptied and by a lancing operation, the spaces between tubes are freed of foreign deposits. Still, there may be sludge remaining between the tubes in the sideways direction angled downward. Therefore, it is necessary to evaluate the overall contour of the sludge accumulated at the bottom of the tubes. Also, determination of the sludge distribution prior to cleaning can be useful for evaluating steam generator design and operation.

According to the present invention, an ultrasonic probe PB is mounted at the end of a ribbon-like probe carrier PC of sufficient stiffness to carry its own weight and that of the probe, while having the ability to bend out of its own plane. The probe carrier is passed into the aisle through the handhole and bent at 90°, in front of a lane defined by two adjacent rows of tubes. To support and bend the probe carrier in front of a lane, a carriage has been specially designed and arranged for precise positioning successively before each lane of tubes. The probe is, thus, carried by the bent portion of the probe carrier into the particular lane at successive distances of penetration in the horizontal plane. The distance to the surface of the sludge is thus measured at each point. This is done ultrasonically after the vessel has been filled with water up to about 0.25 inch below the center line of the handhole. The immersed probe transmits ultrasonic pulses downward from a transducer element mounted underneath. The pulses are reflected from the sludge surface. The frequency is selected for good reflection, or scattering, from angled surfaces, taking into account the sludge particle size distribution, and with a narrow beamwidth. Knowing the speed of sound in water, the distance between the transducer and the reflection surface can be readily determined by electronically measuring the time between the transmitted and received pulses. In order to increase the accuracy of the system a second transmitting and receiving transducer element directs a pulse upward to detect the water surface. By adding the signals of the upward and downward measurements, thus correcting for the probe height, a measurement is provided by reference to the water surface. Still sludge may have remained between the tubes at an angle to the direction of lancing. In order to detect such accumulations, the probe is provided with two additional transducer elements. These are positioned so as to send the ultrasonic signal sideways and at an angle downward between the tubes on each side of the lane. This signal is also added to the upward signal to remove the dependency on the absolute position of the probe. Finally, a signal is transmitted by a front transducer element in the forward direction to provide information regarding the limit position in the tube lane at which to reverse the direction of travel as the probe approaches the wall of the vessel.

FIG. 1 also shows the carriage CR comprising an overhead chariot OC mounted with rollers on a track consisting of a support structure SS. Structure SS is horizontally disposed in the center aisle of the vessel and abuts by its end against a vertical pipe CVP at the very center of the tube array. The chariot is connected by a connecting piece CP to a platform PF held below the support structure SS. Platform PF serves as a guider for deflecting the probe carrier PC at 90° from the aisle for a given position of the carriage along its track. Location of the carriage CR on the track is accomplished through adjustable eccentric cam follower bearings which allow for field adjustment of fit and alignment. Bearings are provided on the top and bottom to guide the overhead chariot OC and on the side to limit sideways motion. Rollers are also provided within the platform PF to align the probe carrier and provide free motion. Within the platform PF is located a 1.25 in. diameter roller with four 0.25 in. diameter rollers located away from its periphery in a 90° turn for entry between the tubes of the generator.

Figure 2:
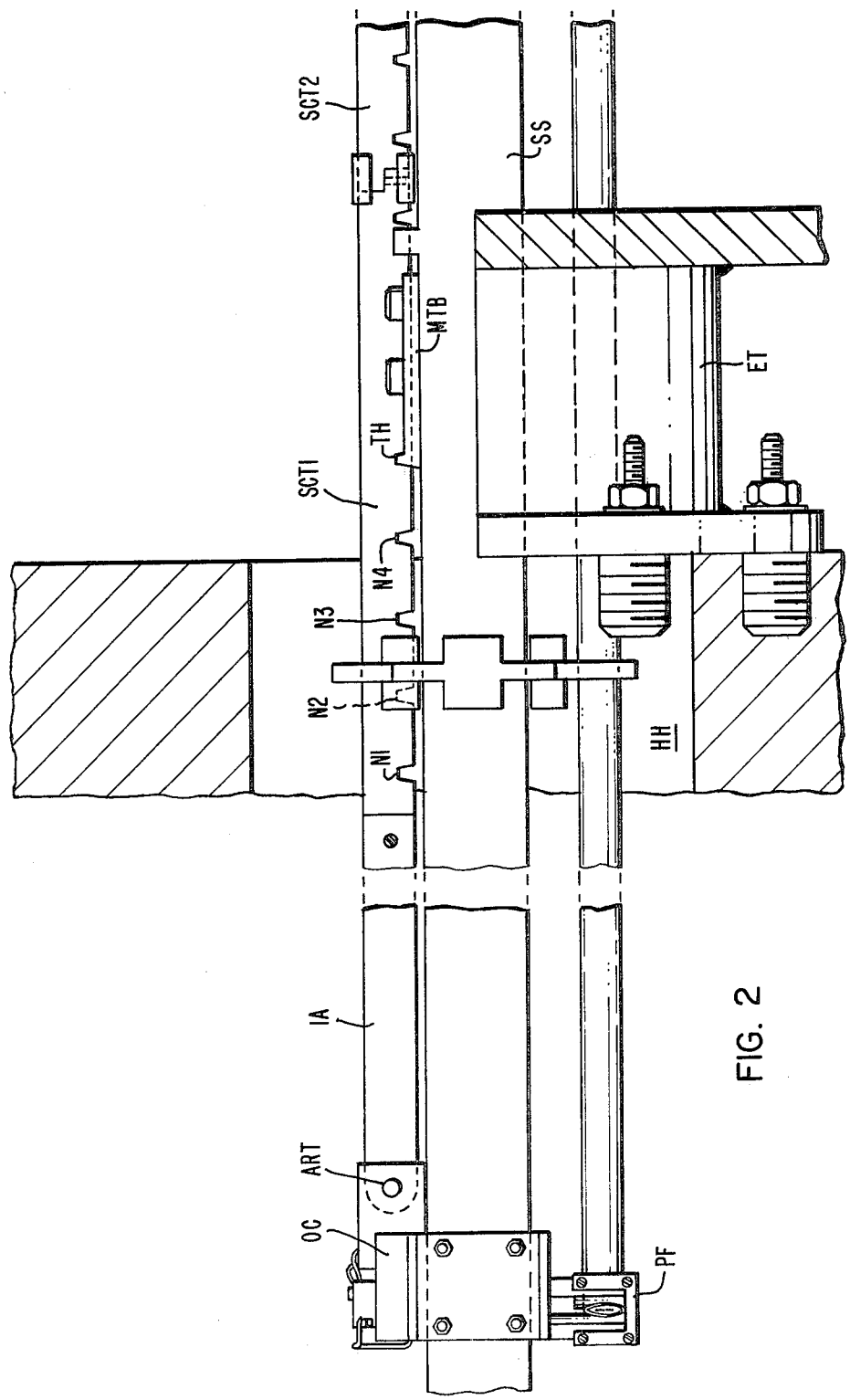
FIG. 2 is a partial view of the carriage, track and probe carrier which are part of the apparatus according to the invention, on the side of the handhole of the vessel containing the array of tubes of FIG. 1.

As shown in FIG. 2, an indexing arm IA articulated at ART is used to move and locate the carriage along its track. This arm, made of several sections SCT1, SCT2, etc. –, is pivotally attached to the carriage and is positioned by means of an adjustable master tooth block MTB which is mounted on the track outside of the handhole HH. The arm is adjusted, via the master tooth, to the first tube position so that the first notch N1 engages tooth TH of the master tooth block. Then, the accurately machined notches in the arm can be selected for any given tube lane under measurement. The arm, like the overhead track, breaks down into sections for limited space installation and operation as well as for portability.

Figure 3:
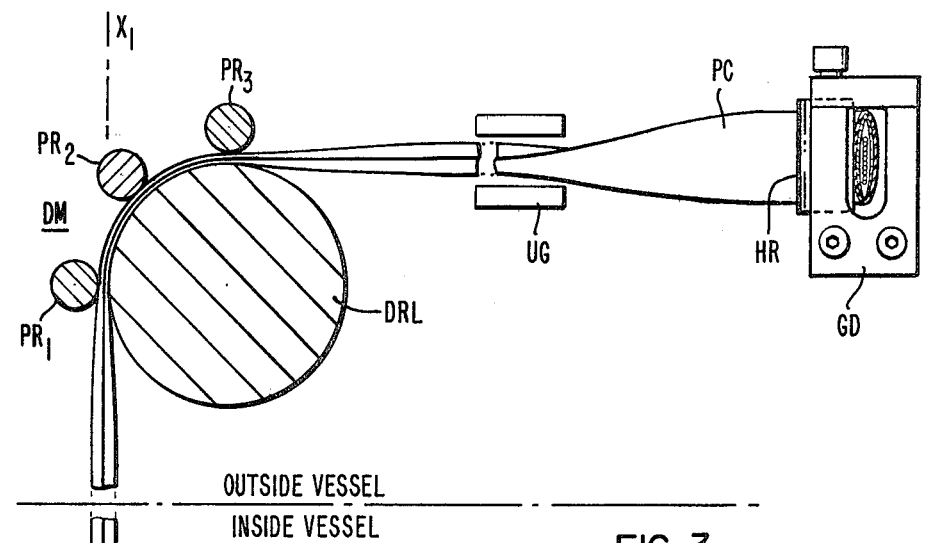
FIG. 3 is a schematic view of the probe carrier of FIGS. 1 and 2 as it is being fed through the wall of the vessel and passed edge up in the L-shaped path of a platform associated with the carriage of FIGS. 1 and 2.
Figure 3:
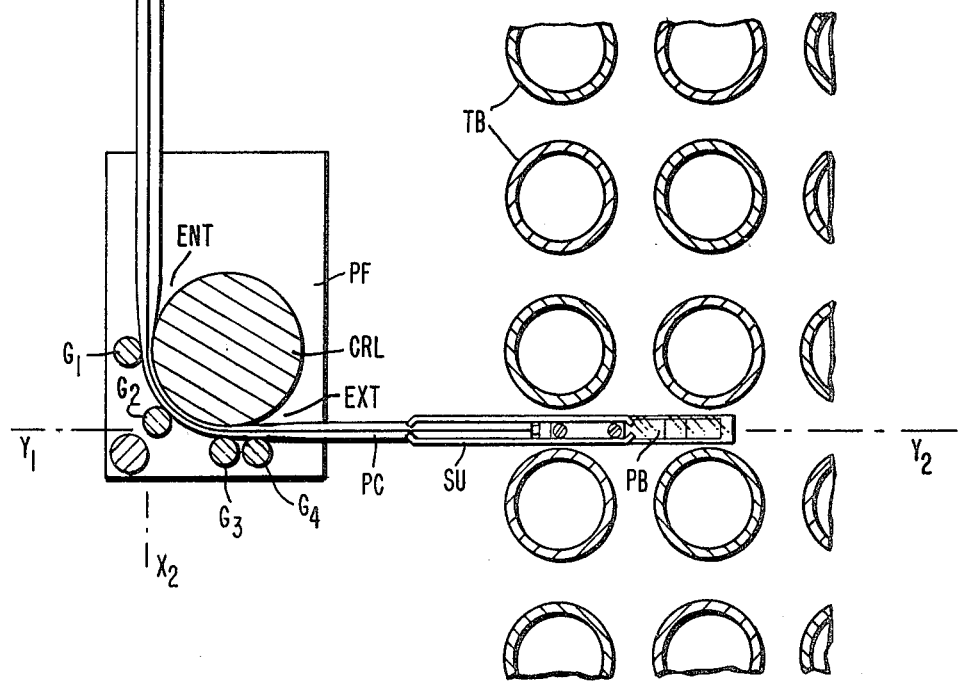

FIG. 3 shows the probe carrier PC in the L-shaped path of the platform PF of carriage CR. The carriage provides horizontal motion along the axis $X_1X_2$ in front of a series of regularly spaced rows of aligned tubes TB defining parallel lanes. The platform has four 0.25 in. guider rolls, two ($G_1,G_2$) associated with the entry ENT of the platform and the axis $X_1X_2$ and two ($G_3$, $G_4$) associated with the exit EXT and the orthogonal axis $Y_1Y_2$. These axes define, about a 1.25 in. diameter central roller CRL, an L-shaped passage from the entry ENT along the axis $X_1X_2$ and the exit EXT along the axis $Y_1Y_2$. The ribbon-like probe carrier PC is inserted, one edge up the other down, into the L-shaped passage of platform PF so that it can glide forward from the entry ENT to the exit EXT while being bent at a right angle under the effect of external guiders $G_1$-$G_4$ and central roller CRL.

As shown in FIG. 3, the probe carrier is moved by a drive mechanism DM including a drive roller DRL introducing friction on the ribbon-like probe carrier, as the carrier is being pressed against drive roller DRL by three peripheral rollers $PR_1$, $PR_2$, $PR_3$. The probe carrier is fed or withdrawn depending upon the direction of rotation of the drive roller which is driven by hand or by a motor (not shown). In order to economize on space outside the vessel, the portion of the carrier kept in reserve extends vertically through a guider GD, after it has been bent out of the horizontal plane into the vertical plane by horizontal roller HR.

Figure 4:
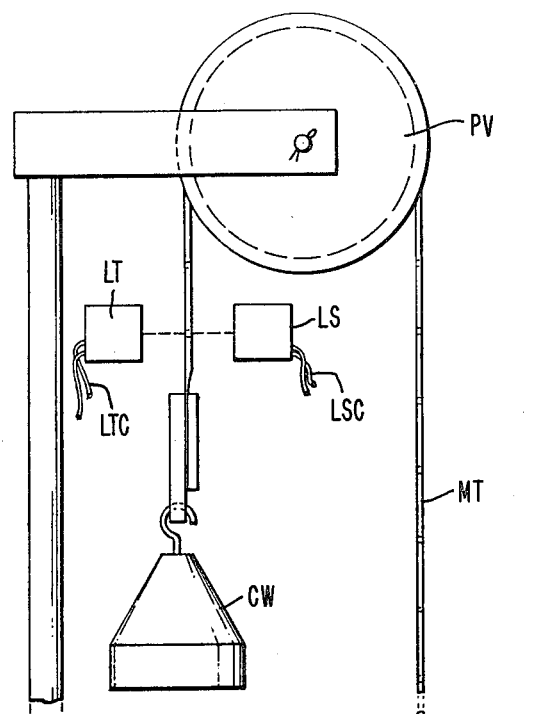
FIG. 4 shows the remote end of the probe carrier anchored by a pulley and counterweight mechanism.
Figure 4:
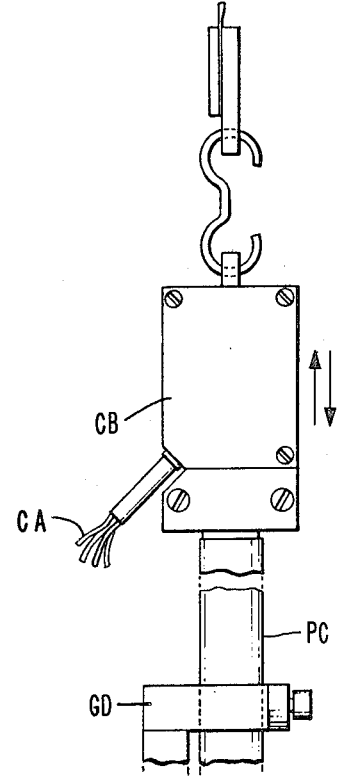

In FIG. 4, probe carrier PC is shown in its vertical position through the guider GD, and anchored into a termination box CB which is hooked to the loose end of a metallic tape MT passed around a pulley PV and maintained by a counterweight CW. The metallic tape MT is provided with a series of holes regularly spaced along its length, and a light source LS, at a location as shown, propagates a ray of light through the successive holes which is detected by a light detector LT placed on the opposite side. Thus, a series of pulses are generated, the number of which is indicative of displacement of the probe carrier. Shielded cables CA carry the probe connections from the moving termination box CB to a fixed connection box BD (not shown) which is mounted on, or near, the extension tank ET (not shown). These features will be hereinafter considered as part of the overall operation of the system according to the present invention Referring to FIG. 3, platform PF is incrementally positioned so that the horizontal axis $Y_1Y_2$ passing through exit EXT is aligned successively with each lane between adjacent rows of tubes TB. For each such position, probe carrier PC and the probe PB is advanced between the two adjacent rows of tubes TB, then withdrawn until a new positioning of platform PF is obtained. If the platform has been properly positioned between such two rows of tubes, the probe in fact when in motion scans downward of the lane and sideways between the successive tubes of each row. In order to scan a large portion of the vessel's bottom surface, this sludge measuring tool reaches approximately 5 feet along the aisle and traverses about 5 feet in a direction at 90°. This procedure is performed in the right and left directions successively from two opposite handholes HH along the aisle down to the central vertical pipe CVP at the center of the vessel (FIG. 1). While distance is measured in terms of travel time, sound velocity must be known accurately.

The sludge depth is determined by the following formula:

$$S=(h-a)-(d+u) \quad (1)$$

where h is the depth of water from its surface, a is the vertical spacing between a transducer element in the probe facing upward ($T_1$ on FIG. 7) and a transducer element in the probe facing downward ($T_4$ on FIG. 7), d is the distance from the downward transducer element down to the sludge surface, and u is the distance from the upward transducer element up to the water surface. Distances d and u are distances actually measured ultrasonically. The first term (h−a) is a constant for each installation and can be preset into the electronics.

Figures 8, 9:
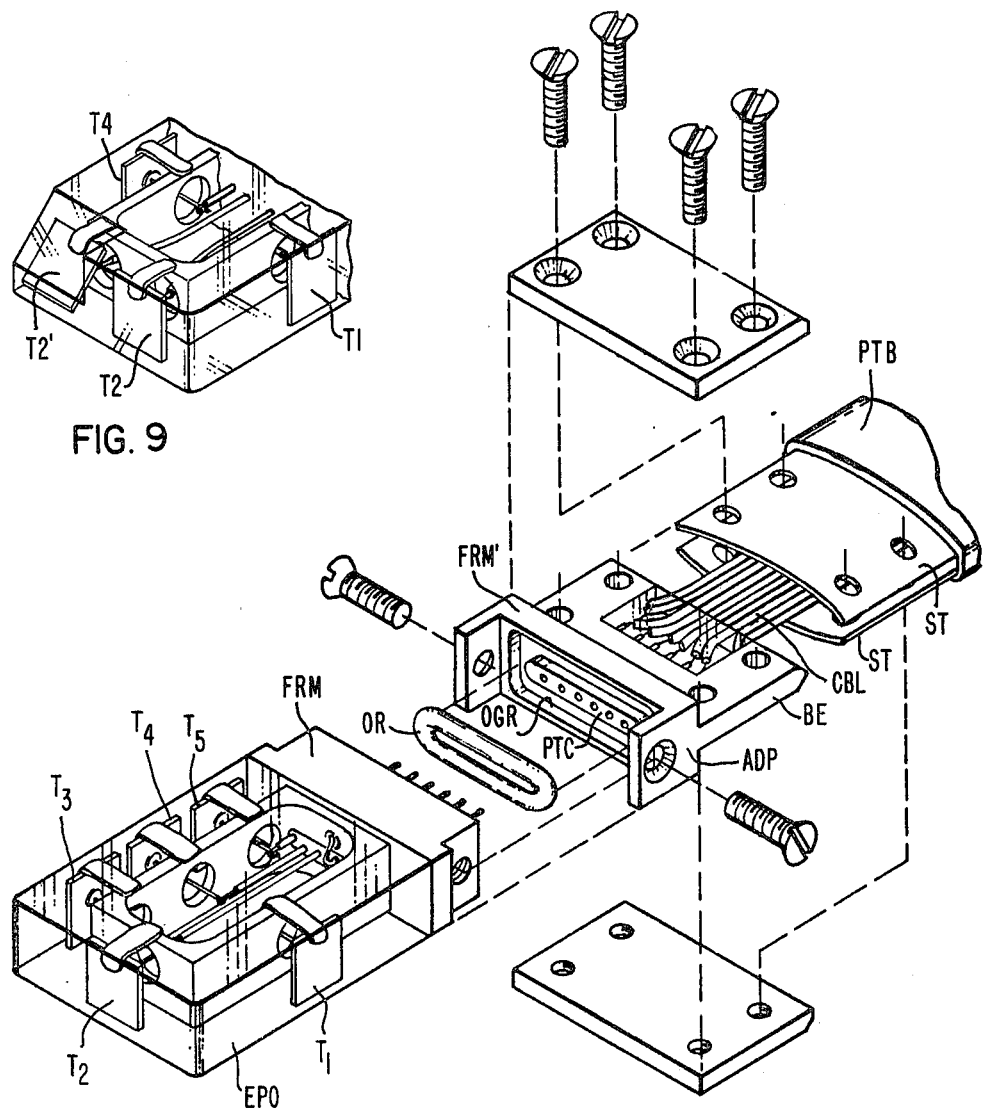
FIG. 8 is an exploded view of the probe assembly of FIG. 7.
FIG. 9 shows another embodiment of the probe head of FIGS. 7 and 8 in which a special transducer element has been placed in front which is oriented at an angle toward the line of tubes for counting past each tube.

Since sludge can possibly be found accumulated between tubes sideways with respect to the direction of water lancing, which is also the probe direction of travel, two additional transducer elements ($T_3$, $T_5$ on FIG. 7) are provided on the probe. These are aimed, one slightly to the right (about 3°), the other slightly to the left at an angle, (also about 3°). Distances measured by these transducer elements would be substituted for d (down) in equation (1) in order to obtain sludge depths for such sideways detection. A transducer element ($T_1$ on FIG. 7) is provided in front of the probe for the purpose of ultrasonically measuring the distance ahead between the probe and the vessel wall. The latter transducer element can be used to reverse probe travel in the lane when the probe comes within a given minimum distance from the wall. Conceivably, the distance to the wall could be measured continuously and the output used as a probe position input to a display device. An alternative method consists in using a transducer element $T_2'$ mounted in the probe and aimed sideways at an angle (typically 45°) as shown in FIG. 9. When the probe is in motion in a lane, the transducer element scans the tubes ultrasonically, thus determining the distance from the aisle by the tube count. In fact, what appears to be the wall in a steam generator is the inner surface of an inner shell called a wrapper or a shroud.

Figure 5:
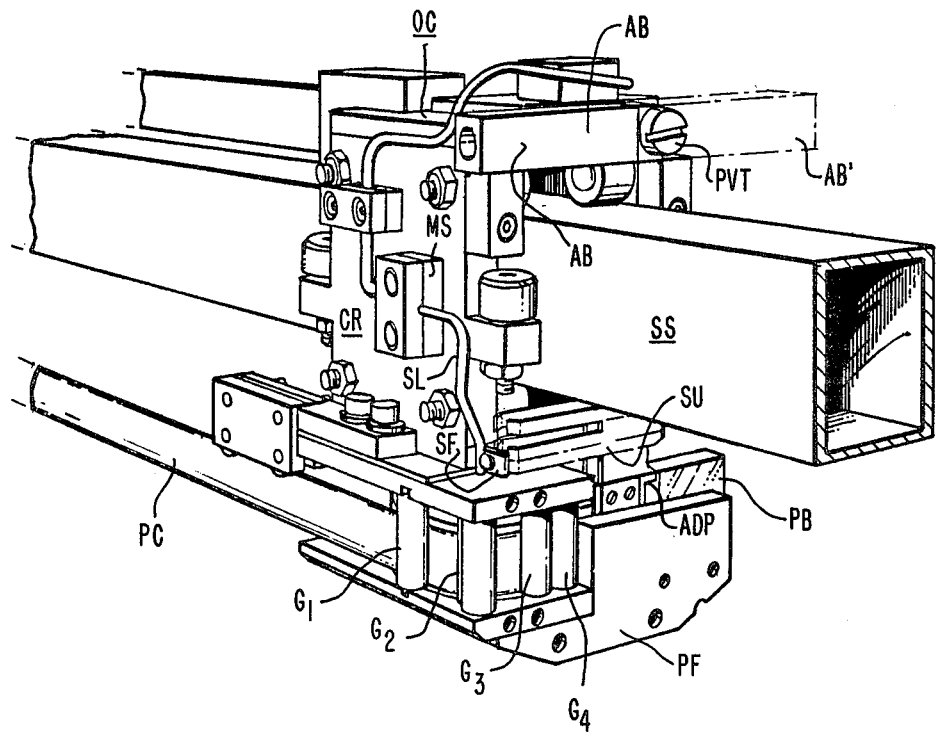
FIG. 5 is a perspective view of the carriage with the platform, the probe carrier being passed therethrough.

FIG. 5 shows carriage CR on its track from a different angle, namely as seen from the quadrant $Y_1Y_2$. A microswitch MS, located on the carriage, is used to automatically stop the probe carrier drive motor after the probe has been cycled and returned to the carriage. This microswitch is activated by the spring steel "wing" SU mounted on top of the probe. FIG. 5 also shows an alignment bar AB which is pivotally mounted at PVT on the overhead chariot OC. Bar AB is used to align the carriage with the first lane, e.g., the lane between the tubes nearest the handhole HH. For this lane with the assist of an extension tool, the bar is pivoted into the dotted line position A'B', e.g., where is falls transversely into the lane, when the carriage is exactly in front of the first lane. At this moment it is known that the carriage is in alignment at its first measurement position.

The support structure SS (FIG. 1) is first inserted into the aisle of the vessel through the handhole HH (shown in FIG. 2). As shown in FIG. 1, the front of the support structure SS is provided with a front support leg FSL which extends out into the vertical position once inside the vessel and comes to rest upon the blowdown pipe BP by means of a "V" block VB. Leg FSL is locked in place by means of a thumbscrew from the handhole. Then the carriage is set on its track (SS) with spring loading. The support structure SS is fixed in position at one end by the center vertical pipe CVP and the blowdown pipe BP, and at the other end, near the handhole, by the drive mechanism DM (FIG. 3). The support structure SS is fabricated from 1.5×1.5 square tubing which breaks down into sections that snap together for easy installation. Structure SS serves as a support for both the overhead chariot OC and the indexing arm IA. Thus, the probe carrier PC is guided, supported and positioned by the mechanical combination of the carriage CR with its platform PF and of the support structure SS.

Carriage CR is first disassembled in order to provide free access for probe carrier PC to the L-shaped path of the platform PF. Referring again to FIG. 3, with the probe PB already mounted at the end of the probe carrier PC, the probe carrier is set upright in place within the platform PF, namely past guider rolls $G_1G_2$ and $G_3G_4$, thus bent at 90° within platform PF. The probe carrier is fed by the drive mechanism DM. When the carriage is assembled, the platform PF, containing the probe carrier PC, and the overhead chariot OC above it, are united by the intermediary connecting piece CP. To the overhead chariot OC is rigidly connected an index arm IA used to position the carriage back and forth on its track. Thus, the carriage is put on the track of the support structure near the handhole and rolled on its track by means of adjustable eccentric cam follower bearings.

Referring again to FIG. 2, the index arm IA is provided at regular intervals with notches $N_1$, $N_2$, $N_3$, etc. which match a tooth TH of a slidable master tooth block MTB which can be anchored by shoulder bolts to a mounting which is part of the support structure SS. The index arm with its extensions extends outside of the handhole. After the index arm has been positioned with the carriage in alignment with the first lane of tubes, as earlier explained, the master tooth block is adjusted so that it matches the first notch $N_1$ of the index arm. The shoulder screws are then tightened in order to lock the master tooth block in place. The distance between notches is equal to the horizontal spacing of the tubes from axis-to-axis, along the aisle. When the index arm is pushed forward so that the second notch registers with the master tooth of MTB, the carriage will have been brought in alignment with the second lane. When necessary, the index arm is lengthened by adding one of several sections at the extremity near the handhole which add up to span the entire radius length of the tube bundle in the aisle.

To enable the probe to be operated under water, an extension tank ET (FIG. 2) is bolted onto the handhole HH. This tank allows the water level in the steam generator to be raised approximately to the centerline of the handhole and also serves as a base for the probe carrier drive mechanism DM (FIG. 3). The rear of the carriage track fastens to a support block which allows for adjustment up, down, left and right.

The probe carrier drive assembly is schematically shown in FIGS. 3 and 4. The probe carrier is held at one end by a counterweight CW, then passes vertically downward into a guider GD then around a guide roll GR from which it emerges in the horizontal plane. The probe carrier is then passed through an upright guide UG and twisted at 90° looking towards a drive roller DRL. The drive roller DRL consists of a 2 in. diameter rubber-faced roll with an abrasive mesh glued to the rubber. The drive roller is driven through three fiber gears by a synchronous motor and planetary gear unit (not shown). Output speed of the planetary gear unit is 16.6 RPM with the drive roller speed being 13.4 RPM, which gives a linear speed of 1.4 in/sec for the probe a speed which has been found to be most favorable. Torque at the drive roller is approximately 480 oz.in.

Figure 6:
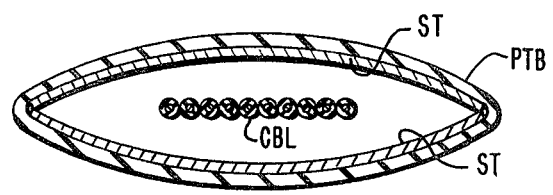
FIG. 6 is a cross section of the probe carrier and the central conductors contained therein.

Referring to FIG. 6, the probe carrier is shown in cross section. It consists of an assembly of two steel tapes ST disposed face-to-face on their concave side and enclosed within a plastic heat-shrinkable tubing PTB shrunk against them. Between the two steel tapes, the space accommodates a flat insulated cable CBL transmitting over six wires the signals derived to and from the probe. Thus, the electrical cable is captured and protected by the tapes. The assembly also provides flexibility for lateral bending while offering sufficient stiffness in the plane of the probe carrier. This is also an arrangement which is easy to construct, inexpensive and replaceable. Indeed, the probe carrier, or at least its plastic tubing PTB may have to be replaced periodically.

Figure 7:
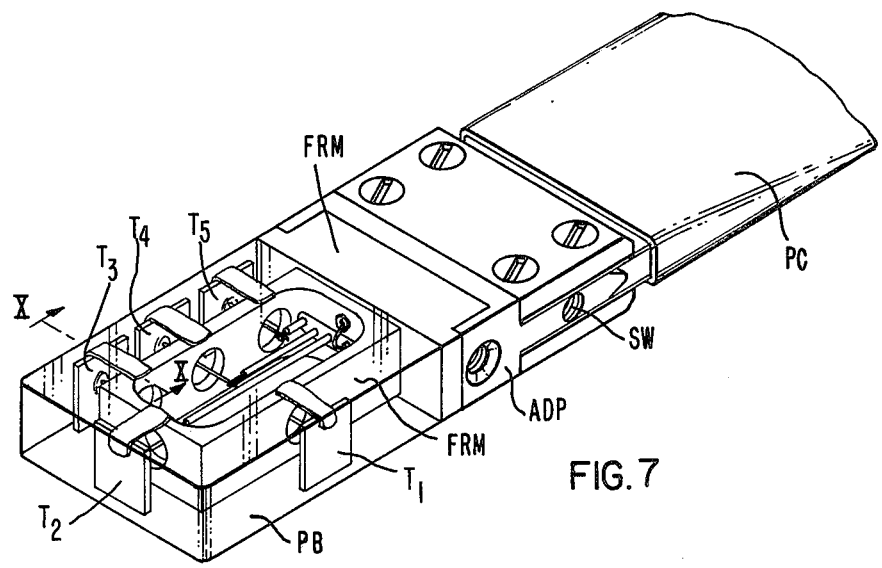
FIG. 7 is a view of the probe attached to the active end of the probe carrier showing the probe assembly with its probe head having five transducer elements and an adaptor member interconnecting the probe head and the probe carrier.

The construction of the probe is illustrated by FIGS. 7, 8 and 9. FIG. 7 shows one embodiment of the probe assembly mounted at the end of the probe carrier. FIG. 8 is an exploded view of the parts assembled in the embodiment of FIG. 7. This probe design is unique and specially intended for the particular application described. An adaptor ADP at the rear of the probe PB provides an intermediate connection with the electrical cable CBL and the probe carrier PC. It also serves as support for a stabilizing spring steel "wing" SU fixed by means of a screw in tapped hole SW. The spring steel "wing" SU of FIG. 5 serves two functions: to keep the probe aligned in its lane between the tubes and to activate through a lever SL a microswitch MS when the probe, while being withdrawn, reaches the limit of its travel back into the carriage, e.g., when the tip of the "wing" hits the end SF of the lever SL. The adaptor has an electrical connector PTC (shown in FIG. 8) for quick replacement and interchangeability of the probe carrier and the probe and to avoid handling integral long wires during fabrication of the probe. A mating connector is provided in the probe.

The assembly of the probe and the adaptor is acoustically, mechanically, and electrically complete and requires only the means of positioning it in the steam generator in order to function as a sludge level detector. Positioning and support are provided by the probe carrier PC. The probe and probe carrier assembly could be considered, from the user's viewpoint, as a basic unit because it is pre-assembled and can be installed and removed as a unit.

In this embodiment, the probe (FIG. 7) contains five transducer elements $T_1, T_2, T_3, T_4$ and $T_5$ facing respectively in the up, forward, down-right, down, and down-left directions, as shown clockwise around an internal grounded frame FRM starting with the $T_1$ element that is seen face-on in the figure. Each element is a 0.195 in. square plate of lead zirconate titanate piezoceramic, having a thickness resonant frequency of 5 MHz. Connections from the rear electrode surface of each element are brought to pins on the connector (See FIG. 8). The front electrode of each element is connected by coatings of conductive epoxy to the aluminum frame FRM, thus providing a common ground for all elements (wires could also be used). A sixth pin on the connector is connected, by means of a wire and a conductive bond, to the frame.

Referring to FIG. 9, another embodiment of the probe head is shown which is similar in many respects to the embodiment of FIGS. 7 and 8, except that, transducer elements $T_3$ and $T_5$ are omitted and another transducer element $T'_2$ is added. Transducer element $T'_2$ is inclined relative to the front face of the probe and oriented toward one side of the probe carrier. In this fashion, transducer element $T'_2$ transmits to, and receives ultrasonic pulses directly from, the tubes which are aligned on one side of the lane, while the probe is travelling in the lane. The electronic circuit counts pulses which are indicative of so many tubes passed during the motion, so that the distance of travel is known and can be instantaneously recorded and correlated with the measurement data.

The adaptor ADP has a frame FRM' which mates with the frame FRM of the probe. Both frames are metallic, and to the ground potential. The adaptor ADP contains the mating connector for the probe and provides for connection to the cable and to the probe carrier. The exploded view (FIG. 8) shows the relationship of the various parts. The 15 ft. long flat cable CBL is permanently attached and sealed to the adaptor and it runs through the entire length of the carrier to a termination at the outer end of the carrier. Only six wires are needed for electrical connections but all ten wires on the cable are used in order that the cable will lie flat within the space defined by the two steel tapes ST. The outer two wires on both sides are conductively bonded to the adaptor to provide additional ground conductors. These outer wires also act as buffers to prevent damage to the six needed wires. Each wire is stranded A.W.G. 30 with an overall thickness of 0.030 in.

The plug-in arrangement, as earlier said, allows the probe to be reused if the carrier wears out, or if a wire breaks. It also has advantages in probe construction by avoiding handling difficulties caused by a long cable. In the adaptor, the connector outer side surface serves as the inner surface of a rectangular O-ring groove OGR, the outer surface being provided by a machined recess. A size 010 O-ring OR provides a water seal.

The back end BE of the adaptor is made as thin as possible (0.090 in.), considering space requirements for the connector and wires, in order to minimize the restriction on probe carrier flattening close to the adaptor. The present design allows the probe assembly to be fully retracted into the supporting platform PF.

Figure 10:
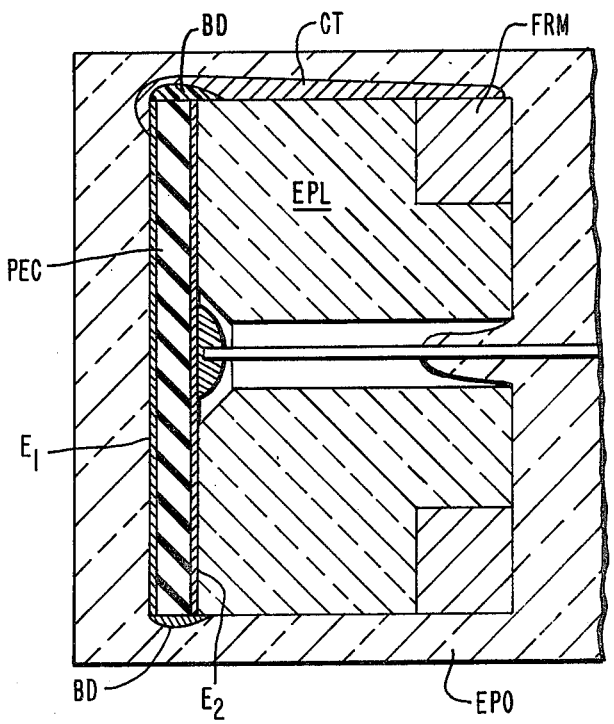
FIG. 10 is a cross section of a transducer element embedded in plastic material with special connections therethrough for the opposite electrodes.

As shown for one transducer element in FIG. 10, the assembly of two electrodes $E_1$, $E_2$ on two opposite faces of a piezoelectric cell PEC is mounted on an epoxy layer EPL but not bonded to it except around the edges at BD. Thus acoustic loading of the rear element surfaces is minimized. Electrical connection is by wire WR at the rear from electrode $E_2$ to the corresponding pin in the connector and by a conductive tongue CT for the grounded electrode $E_1$, in relation to the grounded frame FRM of the probe. Encapsulation of the probe in epoxy EPO is done in several steps, then the outer epoxy surface is machined to final dimensions. Exclusive of the connector pins, the probe measures about 1 in. long, 0.75 in. high, and 0.25 in. wide. The epoxy face thicknesses over each element is 0.030 in. (slightly more over the slanted elements).

The function of the electronics is basically to generate a transmit pulse, detect the arrival of the echo from the sludge or other surface of interest, and produce an output (e.g., D.C. voltage) proportional to the travel time and hence the distance. Additionally the electronics should combine certain outputs, specifically those representing upward and downward distances, and account for water depth so that the sludge depth is displayed. The basic functions must be provided for each transducer element either by switching one set of circuitry among the elements or by having a separate set for each element.

Separate transmitting, receiving, and readout circuits are used for the various transducer elements rather than time-sharing one set of circuitry. This approach simplifies the switching and allows each circuit to be adjusted for a specific element, a specific range, and specific reflection characteristics. Switching is electronic and hence rapid and capable of various operating sequences. Time-sharing, if used, would require the switching of transducer elements and various circuit components, which probably would involve relays.

Figure 11:
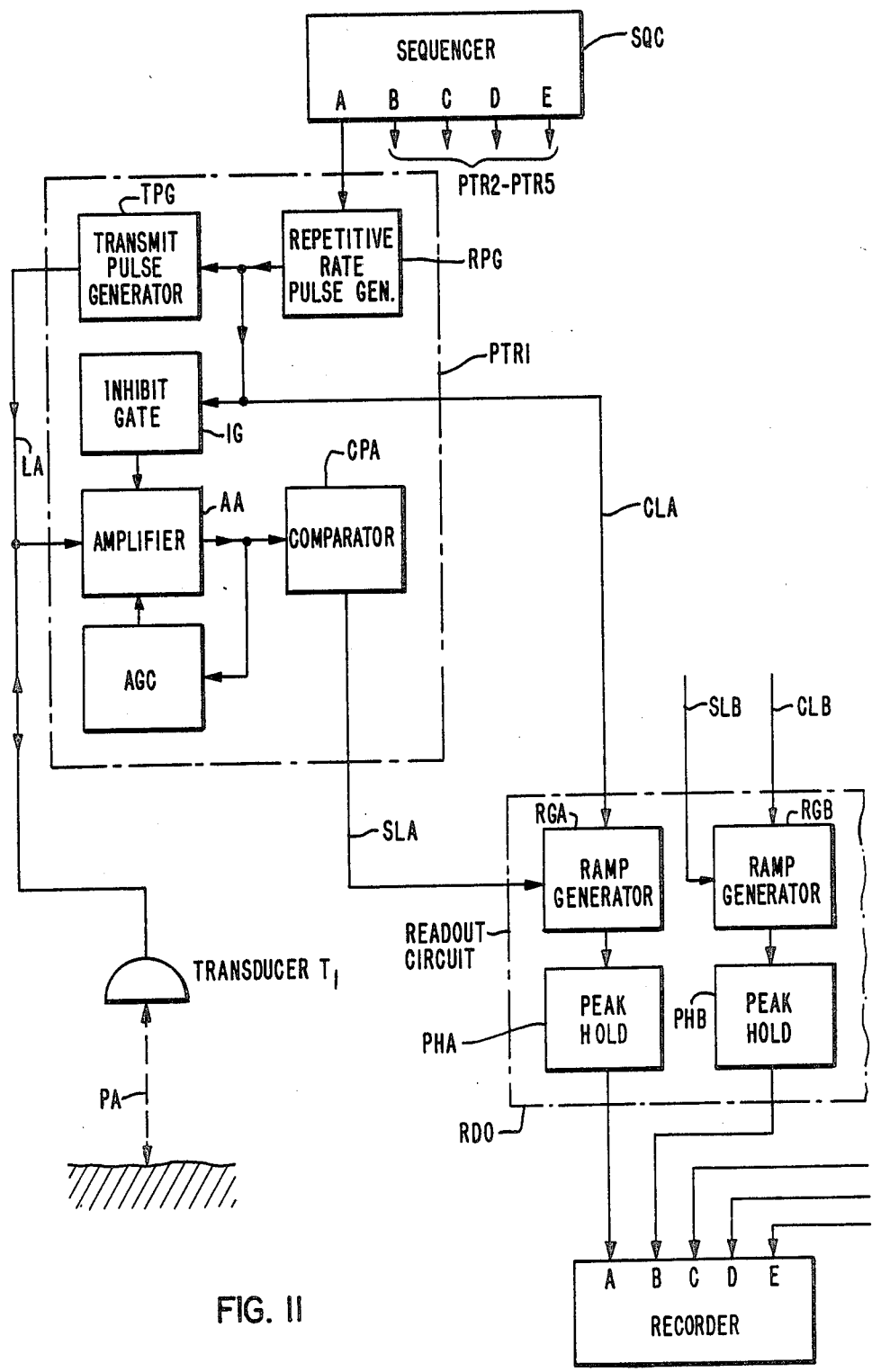
FIG. 11 is the electronic circuit for the generation and reception of ultrasonic signals through the medium and for the detection and recording of relevant data.
Figure 12:
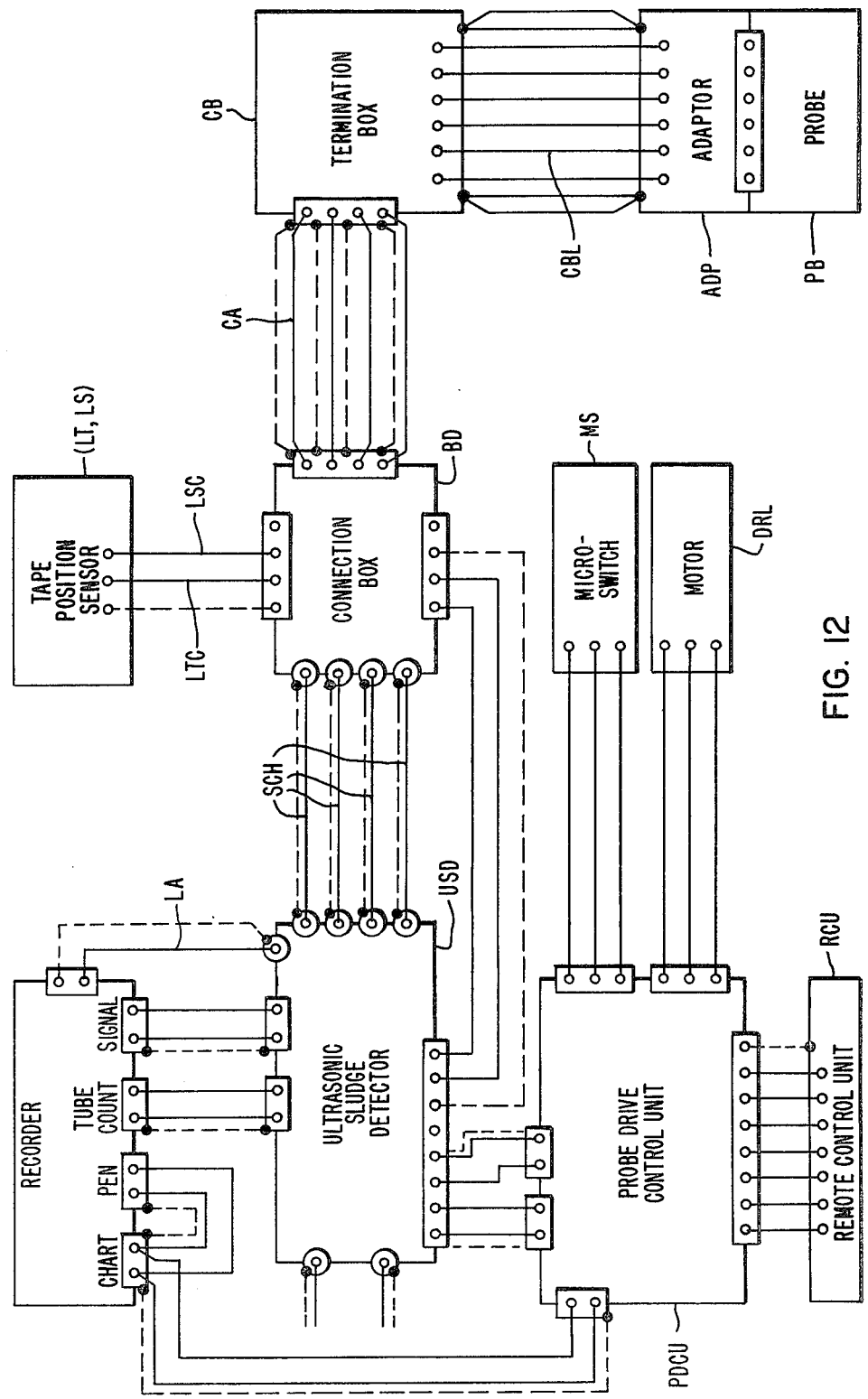
FIG. 12 shows the wiring arrangement between the probe carrier and the electrical system associated with the apparatus according to the invention.

A block diagram of the electronic circuitry is shown in FIG. 11. FIG. 12 is a wiring diagram of the overall electrical system.

Referring to FIG. 11, the ultrasonic sludge detector section comprises, for example, five pulse transmitter-receiver circuits $PTR_1$-$PTR_5$ and one readout circuit RDO associated with the five transducer elements $T_1$-$T_5$ of FIGS. 7 and 8 under command of a sequencer SQC having five steps A-E.

The pulse-transmitter-receiver circuit $PTR_1$ associated with transducer $T_1$ is shown including a transmit pulse generator TPG triggered by a repetitive rate pulse generator RPG when actuated by step A of sequencer SQC. The generated pulse is applied via line LA to transducer $T_4$. The outputted ultrasonic pulse is transmitted through path PA into the medium and reflected back through the same path from the surface of the accumulated sludge. Amplifier by amplifier AA, the electrical pulse returned via line LA from transducer $T_1$ is conveyed as an effective detected signal whenever the returned pulse exceeds the threshold of a comparator CPA. The time delay between transmitted and reflected ultrasonic signals of path PA is determined in relation to the time basis of a ramp generator RGA triggered via line CLA from the repetitive rate pulse generator RPG and stopped via line SLA from comparator CPA. The contour of the scanned surface of the accumulated sludge is recognized as the envelope of the successive outputs of ramp generator RGA by a peak-hold circuit PHA, for the respective positions of the probe PB inside a lane. Readout circuit RDO contains similar circuits (RGB, PHB), . . . (RGE, PHE) in relation to transducer $T_2$-$T_5$ and the associated pulse transmitter-receiver circuits $PTR_2$-$PTR_5$. Thus, readout circuit RDO receives control signals such as (CLB, SLB)-(CLE, SLE). When sequencer SQC triggers transducer $T_1$-$T_5$, recorder RCO receives the output voltages from the respective peak-hold circuits PHA-PHE, and combines certain received signals to generate measurement data in accordance with equation (1). Some signals are used for probe drive control, as described.

In the ultrasonic sludge detector unit, a 500 V maximum transmit pulse is generated at a fixed repetition rate (typically 1 kHz) and applied to the transducer element $T_1$. The transmit pulse generator TPG consists of five fast switching thyristors (acting as one device) in series which discharge a capacitor to shock-excite the transducer element. The transducer is also connected to the receiver, which amplifies the small received signal and detects its arrival time in terms of the threshold crossing. The received signal appears as a short burst of 5 MHz oscillations. The receiver is protected against the transmit pulse which is also applied to its input. A time gate IG, generated each repetition period, inhibits the amplifier AA except during an interval in which the signal is expected to occur. Thus the transmit pulse and other unwanted signals, such as the reflections from various surfaces, have no effect.

Automatic gain control (AGC) is used over a considerable range of received signal magnitudes. The peak of the received signal envelope is sensed and used to adjust the amplifier gain. If no signal is present, the gain goes to maximum. Comparator CPA is used to mark the arrival of a received signal by generating a pulse when the amplified signal voltage instantaneously crosses the threshold level.

In the readout circuit RDO, a constant slope ramp is started by the transmit pulse and terminated by the comparator pulse. Thus the peak voltage of the ramp is proportional to the travel time and hence distance. The peak voltage is transferred to a storage circuit which holds this value, which is the output voltage, until the next peak occurs. The ramp is reset and restarted for each transmission.

For recording and displaying the output, a strip chart recorder is used. The strip chart recorder runs at constant speed and requires that the probe travel at constant speed (i.e., no-slip drive) for the chart to correctly indicate horizontal position. The drive mechanism described hereabove does meet the no-slip requirement. Probe horizontal position is sensed, however, and a signal proportional to position could be used to drive the chart if flip became a problem.

Successive traverses between rows would appear one after the other on the chart. Marking to identify each traverse could be manual or automatic. Chart speeds should be consistent with desired chart lengths for each traverse. Successive chart traces can be physically or graphically arrayed side-by-side to produce a replica of the entire sludge surface.

Referring to FIG. 12, the wiring diagram as used in its most complete embodiment is shown with the connections between the various circuit boxes, and functional units. This wiring diagram is based on the embodiment of FIG. 10, where only four transducer elements (up, down, front and side) are in use. Thus, probe PB and adaptor ADP are connected via wires CBL to the termination box CB of FIG. 4. From box CB the connective wires are extended via shielded cables CA to another connection box BD distributing electrical information and commands between 1) the tape position sensors (LT, LS of FIG. 4) via a shielded cable (LTC, LSC), and 2) transducer signals by shielded cables SCH to and from the ultrasonic sludge detector unit USD (FIG. 11). The probe drive control unit PDCU controls the motor actuating the drive roller DRL (FIG. 3) and responds to the microswitch. The recorder (FIG. 11) is also shown in FIG. 12 connected to the output of the ultrasonic sludge detector section USD, and to various chart control and auxiliary signals, some of which originate at unit PCDU. The remote control unit RCU duplicates the controls and indicators of PCDU for an operator close to the handhole HH (FIG. 2) but remote from PCDU.

We claim:

1. Apparatus for ultrasonically measuring sludge accumulations between the tubes of a heat exchanger having a plurality of tubes straddling a central vertical aisle defined between vertical portions thereof, and contained within a vessel filled with water as a medium for propagating ultrasounds, comprising:
   a probe carrier of elongated shape having rigidity in one plane and being bendable out of said plane;
   an ultrasonic probe head mounted at one end of said probe carrier;
   electrical conductors for said probe head carried by said probe carrier;
   an elongated support adapted to be mounted horizontally within said aisle and on said vessel;
   a carriage mounted for movement at successive positions along said elongated support;
   guider means on said carriage defining in the horizontal plane an L-shaped path between an entry and an exit thereof;
   said probe carrier being passed in said one plane and in a flexed condition across said entry and exit of said guider means into said L-shaped path;
   means for feeding said probe carrier forward through said guider means in relation to one of said carriage positions and for extending said probe head horizontally into a lane defined at 90 degrees to said aisle between adjacent vertical portions of tube for said one carriage position;
   said probe head being adapted to generate ultrasonic signals in said lane through said medium toward said sludge accumulations and to detect ultrasonic signals reflected back therefrom when positioned by said feeding means at a given distance inside said lane; and
   means connected at the other end of said probe carrier and to said electrical conductors for deriving an indication of the depth of said sludge accumulations in relation to successive said carriage positions and under the operation of said feeding means for each corresponding lane.

2. The apparatus of claim 1 with said probe head having at least one transducer element for vertically transmitting downward and receiving ultrasonic signals upward when said probe head is travelling in said lane.

3. The apparatus of claim 2 with second and third transducer elements for transmitting and receiving ultrasonic signals sideways and downward on the two respective opposite sides of said probe head when travelling in said lane.

4. The apparatus of claim 3 with another transducer mounted on said probe head and oriented sideways for ultrasonically scanning tubes while travelling in said lane and for deriving a count representative of distance of travel, said indication of the depth of said sludge accumulations being derived in correlation to said count.

5. The apparatus of claim 1 with a fourth transducer element mounted in front of said probe head for measuring distances ahead of said probe head.

6. The apparatus of claim 1 with said feeding means being operative in the reverse direction to withdraw said probe carrier, with alignment means mounted on said probe head, extending beyond the rear thereof and parallel to said probe carrier for registering with said guider means when said probe carrier is withdrawn from said lane by said feeding means.

7. The apparatus of claim 1 with microswitch means activated by said alignment means for stopping said feeding means in the reverse direction.

8. An ultrasonic transducer assembly comprising:
   a central conductive frame at ground potential;
   a plurality of transducer elements having opposite electrodes and disposed peripherally about said central frame a distance therefrom;
   first electrical connectors between said frame and the electrodes of one polarity;
   second electrical connectors associated with the respective electrode of the other polarity passed through said central frame and isolated therefrom;
   said transducer elements, said central frame and said first and second electrical connectors being embedded within plastic material for maintaining a physical relation therebetween; said plastic material being machined to provide front and lateral faces for said transducer assembly; and plug means at one end of said central frame forming electrical terminals for said first and second connectors.

9. The transducer assembly of claim 8 in combination with an adaptor member;

said transducer assembly and said adaptor member having respective matching faces;

electrical terminals for said adaptor member being provided thereacross;

said terminals of said adaptor member being in a one-to-one relationship relative to said terminals of said plug means and the respective terminals being adapted for mechanical and electrical coupling when said matching faces are engaging each other.

10. The combination of claim 9 in combination with a support containing electrical conductors for said transducer elements;

said adaptor member being mounted on said support; and said electrical conductors being connected to respective ones of said terminals of said adaptor member.

11. The combination of claim 10 with said support being elongated, rigid in one plane and bendable out of said one plane.

12. The combination of claim 11 with said support consisting of two concave metal tapes face-to-face and a shrinkable tube shrunk around said metal tapes to hold the same in relative position; said electrical conductors being isolated and disposed between said metal tapes in the space defined by the concave faces thereof.

13. The combination of claim 12 with means for holding a length of said support in situ at a cornering position of measurement and for deflecting said support at 90° from said cornering position; and means for feeding said support through said holding means to selectively position said transducer assembly at right angle from said cornering position.

14. The combination of claim 9 with said transducer assembly being removable from said adaptor member.

15. Apparatus for bi-dimensionally positioning a probe within an enclosure defined by a vessel wall and in a horizontal plane thereof;

a carrier for said probe;

said carrier being an elongated member of substantial stiffness longitudinally and vertically and having bendability out of the vertical plane;

means selectively positioned a distance from said wall along a first axis for deflecting said carrier along a second axis orthogonally from said first axis; and means for feeding said carrier through said deflecting means to selectively position said probe with said carrier along said second axis.

16. The apparatus of claim 15 with track means mounted across said vessel wall into said enclosure;

said positioned means including a carriage adapted for movement along said track means, said deflecting means being mounted on said carriage;

arm means extending across said vessel wall, parallel to said track means and connected to said carriage for positioning the same a predetermined distance from said vessel wall on said track means.

17. The apparatus of claim 16 with said arm means having a first section connected to said carriage, and a plurality of additional sections removably connected after said first section.

18. The apparatus of claim 17 with said first and additional sections having indicia regularly spaced by the distance between consecutive tubes along the direction of said track means; said track means having a reference member adapted for registering with each of said indicia;

said fixed reference member being initially fixed in position for registration with a first of said indicia when said carriage is positioned in relation to said deflecting means being aligned with a first one of said lanes.

19. An ultrasonic transducer assembly comprising:

a grounded metallic frame, a piezoelectric element having a front and back electrode;

said back electrode being separated from said frame by an isolation spacer having a central opening;

an electrical lead connected to said back electrode through said central opening of said spacer and through said frame;

a peripheral insulation between said front and back electrodes at the periphery thereof;

an electrical connection between said front electrode and said frame externally of said spacer and said frame, spacer, peripheral insulation, electrical connection and front electrode being embedded altogether in an epoxy resin and said epoxy resin being machined to provide front and side faces for the overall assembly.

* * * * *